US008173175B2

(12) United States Patent
Perez Correa et al.

(10) Patent No.: US 8,173,175 B2
(45) Date of Patent: May 8, 2012

(54) ETHANOLIC AND/OR AQUEOUS COMPOSITION OF AN AMMONIACAL SOLUTION OF ALKALINE METAL SALTS OF AZIDE, MAINLY SODIUM AND POTASSIUM

(75) Inventors: Francisco Javier Perez Correa, Santiago (CL); Juan Ormeno Nunez, Santiago (CL)

(73) Assignee: Universidad De Chile, Santiago (CL)

( * ) Notice: Subject to any disclaimer, the term of this patent is extended or adjusted under 35 U.S.C. 154(b) by 353 days.

(21) Appl. No.: 12/086,162

(22) PCT Filed: Dec. 6, 2006

(86) PCT No.: PCT/IB2006/003858
§ 371 (c)(1),
(2), (4) Date: Aug. 5, 2009

(87) PCT Pub. No.: WO2007/066224
PCT Pub. Date: Jun. 14, 2007

(65) Prior Publication Data
US 2009/0324749 A1  Dec. 31, 2009

(30) Foreign Application Priority Data

Dec. 7, 2005 (CL) .................................. 3195-2005

(51) Int. Cl.
*A01N 59/00* (2006.01)
(52) U.S. Cl. ........................................................ 424/722
(58) Field of Classification Search .................. None
See application file for complete search history.

(56) References Cited

U.S. PATENT DOCUMENTS 3,984,227 A * 10/1976 McConnell et al. .......... 504/119
6,852,341 B2 * 2/2005 Rodriguez-Kabana ....... 424/719

* cited by examiner

*Primary Examiner* — Alton Pryor
(74) *Attorney, Agent, or Firm* — Neifeld IP Law, PC

(57) ABSTRACT

The present invention consists of the discovery about an ammoniacal solution of sodium azide ($NaN_3$) or other azide salts that in low concentrations induces the budding of grapevine buds and potentially other deciduous fruit trees with the same efficiency as $H_2CN_2$ makes.

10 Claims, 3 Drawing Sheets

ETHANOLIC AND/OR AQUEOUS COMPOSITION OF AN AMMONIACAL SOLUTION OF ALKALINE METAL SALTS OF AZIDE, MAINLY SODIUM AND POTASSIUM

RELATED APPLICATIONS

This application is a National Stage Application under 35 U.S.C. 371 of International Application No. PCT/IB2006/003858, filed Dec. 6, 2006.

The present invention refers to a composition to release the dormancy or winter recess of buds in deciduous fruit trees, by means of the application of an ammoniacal solution of alkaline metal salts of azide, mainly sodium and potassium.

GENERAL ANTECEDENTS OF THE INVENTION

The deciduous fruit trees require of winter cold to grow normally. The amount of required cold depends on the species and the cultivar and it is genetically determined (Saure, 1985 Dormancy release in deciduous fruit trees. Horicultura Review 7: 239-299). Growth alterations such as scarce and uneven budding, low leaves cover, scarce fruiting and fruits of small size are generated when the winter cold is not enough (Mauget, and Rageau 1988 Bud dormancy and adaptation of Apple trees to mild to winter climates. Act Horti 232: 101-108; Couvillon and Erez, 1985 Effect of level and duration of high temperatureson rest in peach. J. Am. Soc. Hort. Sci 110: 579-581; Balandier, Gendraud, Rageaun Bonhome, Richard and Parisot 1993 for Budbreak delay on single node cutting and bud capacity nucleotide accumulation for ace parameters endo and paradormancy in peach trees in tropical climate. Sci Hort. 55: 249-261). The cold requirement from a species is one of the main factors limiting the fruit trees cultivation of temperate climates in zones of warm winter (Saure to us, 1985 Dormancy release in deciduous fruit trees. Horicultura Review 7: 239-299). It is generally accepted that the deciduous fruit trees must be exposed to low temperatures in order to break the dormancy (Lang, 1994 Dormancy the missing links: Molecular studies and integration of regulatory plant and environmental interactions Hort. Science 29: 1255-1263). The dormancy or winter recess state is a stage of the woody perennial plants development that contributes to survival of the plants under the adverse conditions of the winter. This stage is characterized by the absence of growth of any meristematic tissue (Lang, 1987 Dormancy: To new terminology. HortScience 22: 817-820).

In order to counteract the lack of winter cold needed by the deciduous fruit trees cultivated in zones of warm winter, diverse procedures have been used both is cultural practices and treatments with chemical agents that break the dormancy. The last procedure is more effective than the others and therefore universally used (Saure, 1985 Dormancy release in deciduous fruit trees. Horicultura Review 7: 239-299).

STATE OF THE ART

Diverse chemical compounds have been pointed out as breakers of the dormancy in deciduous fruit trees (Doorenbos, 1953 Review on the literature on dormancy in buds of woody plants. Meded Landbouwhogeschool. Wageningen 53: 1-24): Mineral oils, dinitrated-derived compounds such as dinitrophenol, dinitro-cycle-hexylphenol and dinitro-ortocresol (DNOC), thiourea, potassium nitrate, hydrogen cyanamide. It has also been pointed out that some phytohormones such as gibberellic acid (GA3), indolacetic acid (IAA), kinetine could act breaking the dormancy (Erez and col, 1971 Improved methods of breaking rest in the peach and others deciduous fruit species. J. Amer. Soc. Hort. Sci 96: 519-522). Nevertheless, few compounds have been used in a commercial way.

DNOC both single and mixed with mineral oils have been applied commercially in several parts of the world. For example, in South Africa, DNOC was used for a long time to break the dormancy of apple trees buds (Erez, 1979 oil The effect of temperature on the activity of +DNOC spray to break the rest of Apple buds HortScience 14: 141-142). Nevertheless, because of the high degree of toxicity that presents DNOC, their import and marketing is forbidden at present in some South American countries such as Peru (www.portalagrario.gov.pe). The high toxicity together with the lack of reproducibility of the DNOC applications are factors that have limited their use and marketing strongly.

Hydrogen Cyanamide. According to several authors (Snir, 1983 Chemical dormancy breaking of network raspberry HortScience 18: 713-719; North, 1989 Effect of cyanamide and DNOC/oil on budbreak, yield and fruit size of golden delicious apples S. soil Afr. J. Plant 6: 176-178; Stadler, North and Artificial Lutze 1991 rest-breaking of apricot and plum cultivars using hydrogen cyanamide J.S. Afr. Soc. Hort Sci 1: 9-11; Nee and Fuchigami, 1992 Overcoming rest AT different growth with hydrogen cyanamide Scientia Horticulturae 50: 107-113) the hydrogen cyanamide ($H_2CN_2$) is the most effective alternative to replace DNOC. At the moment, the hydrogen cyanamide is universally used to break the dormancy in deciduous fruit trees. In Chile, DORMEX has been used in grapevines cultivation during more than one decade, as indispensable tool in the production of table grape. The $H_2CN_2$ was firstly commercialized by the German company SKW Trostberg using the name, DORMEX. At the moment, in Chile, the $H_2CN_2$ is commercialized under the registered trademarks of DORMEX (Basf) and NEXUS (Anasac). The $H_2CN_2$ is considered the most powerful and efficient agent that exists to release the buds dormancy at the moment in the world-wide market (Erez, 1987 Chemical control of budbreak HortScience 22: 1240-1243; Henzell, Briscoe and Gravett 1991 Improving Kiwifruit I came productivity with plant growth regulators. Act Horticult 297: 345-350; Or, Nir and Vilozny 1999 Timing of hydrogen cyanamide application to grapevine buds Vitis 38: 1-6). Nevertheless, in spite of the long permanence of $H_2CN_2$ in the market, its way of action still is unknown. According to the manufacturer at biochemical level the main effect of $H_2CN_2$ is the inhibition of the enzyme catalase. This enzyme catalyses the decomposition of hydrogen peroxide ($H_2O_2$) to water and oxygen. Once the catalase activity has been inhibited the plant would lead to detoxicity of the $H_2O_2$ through a sequence of reactions connected to the pentose phosphate pathway that would lead to an increase of the production of nucleotides NAD(P)H reduced that would increase the metabolism and finally would cause the rupture of the bud (www.dormex.com). Nevertheless, the single inhibition of the catalase activity does not explain the $H_2CN_2$ effects on the budding, because experiments with 1,4-triazolamine, a specific inhibitor of the catalase activity, although is able of inhibit the catalase activity in grapevine buds, does not have any effect on the budding (Nir and Lavee, 1993 Metabolic changes during cyanamide induced dormancy release in grapevines Act Hort 329-333). $H_2CN_2$ is a toxic compound, skin and eyes irritant, these symptoms are especially acute in combination with the alcohol ingestion. The European Union (EU) has catalogued the $H_2CN_2$ as a toxic, harmful compound in contact with the skin and eyes and skin irritant. On the other hand, the United States Environmental Protection Agency (USEPA) has classified Dormex and its active ingredient, $H_2CN_2$, in category I (acute toxic). Due to these characteristics rubber clothing and face shield must be used for its application and handling (www.safeùse.com).

According to the exposed arguments, at the state of the art, there is the necessity of developing new agents to break the dormancy which must be accesible, effective, less toxic and could be used in reasonable concentrations.

SUMMARY OF THE PRESENT INVENTION

The present invention consists of the discovery of an ammoniacal solution of sodium azide ($NaN_3$) or other azide salts which in low concentrations induces the budding of grapevine buds and potentially of other deciduous fruit trees, with the same efficiency as $H_2CN_2$.

BRIEF DESCRIPTION OF DRAWINGS

FIG. 2 is a graph showing the effect of different dosages of 1, 1.5 and 2% (w/v) sodium azide in aqueous and 1% ammoniacal solutions on the bud sprout percentage of cv. Thompson seedless grapevine; treatments were carried out on June 22 and a 5% Dormex (w/v) solution was used as a positive control and water as a negative control; and.

SPECIFIC ANTECEDENTS OF THE PRESENT INVENTION

The alkaline metal salts of azide have been used widely in agriculture to control weeds (herbicide), as a defoliant agent and in the control of nematodes and fungi. In these applications the salts of azide are used in high concentration 20-40% (w/v) and go directly to the soil. At the moment, in the U.S.A. a patent exists that claims the use of salts of azide solutions as a herbicide (U.S. Pat. No. 3,984,227 October 1976) and another one that claims the use of salts of azide to control deleterious organisms present in the soil (U.S. Pat. No. 6,852, 341).

Experiments made in the R.M with plants acclimated in greenhouse under conditions of photoperiod and temperature similar to those of the region IV demonstrate clearly that the azide ammoniacal solutions to 1 and 2% reproduce the same effects on the budding as the commercial solution of DORMEX. On the other hand, field experiments made in Vicuña (region IV) during 2003 and 2005 seasons indicated that aqueous and ammoniacal solutions of $NaN_3$ induce the budding of cv. Thompson seedless grapevine buds. The early budding of buds depended on the dose of $NaN_3$, and at the highest dose 2% (w/v), the effects were the same as those of a solution 5% (w/v) Dormex equivalent to 2.5% of a.p ($H_2CN_2$).

Greenhouse Trials

Figure 1:
FIG. 1 is a photocopy of a photograph of bud sprouts showing the effect of 2.5% $H_2CN_2$ (CH) (w/v); 1 and 2% sodium azide and distilled water (control) on cv. Thompson seedless grapevine bud sprout.

The FIG. 1 shows cv. Thompson seedless grapevine plants acclimated in greenhouse under conditions of photoperiod and temperature similar to those of the region III and IV. On Jul. 1, 2002 the plants were treated with DORMEX ($H_2CN_2$ 2.5%) (w/v); sodium azide ($NaN_3$) to 1 and 2% (w/v) in ammoniacal solution to 1% and distilled water as a control. The applications were made in manual way using cotton saturated with the respective solutions until dripping. The budding was evaluated on September 6; this means 66 days after the applications. FIG. 1 shows clearly the inducer effect of $NaN_3$ on the budding of grapevine buds, also shows that the effect depends on the applied dose and that using dose to 2% similar results are obtained to those of Dormex 5%.

Field Trials

Figure 2:
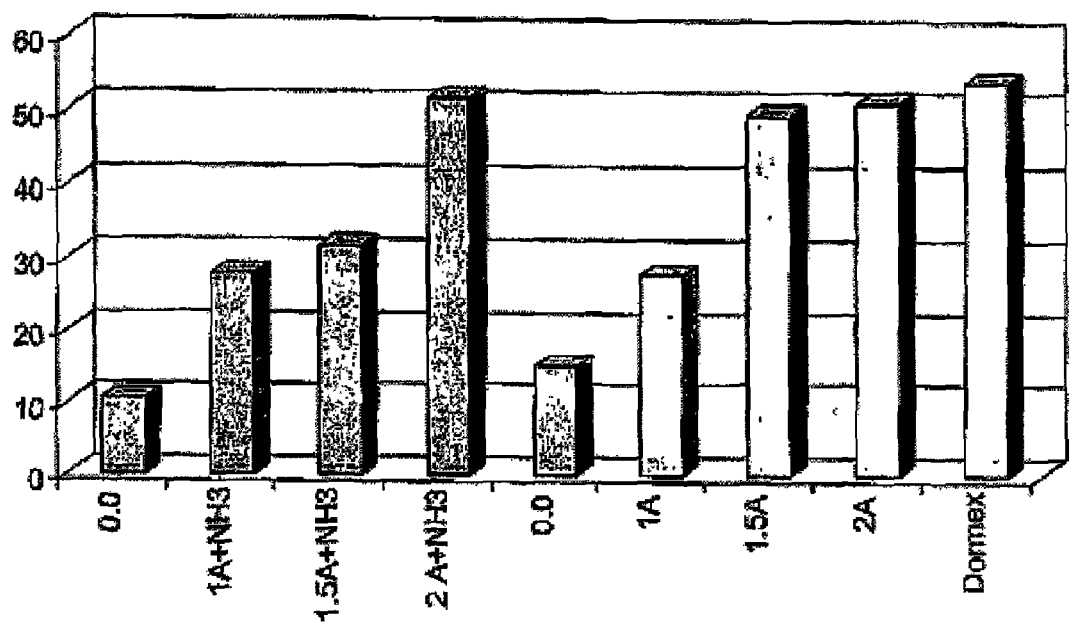
Figure 3:
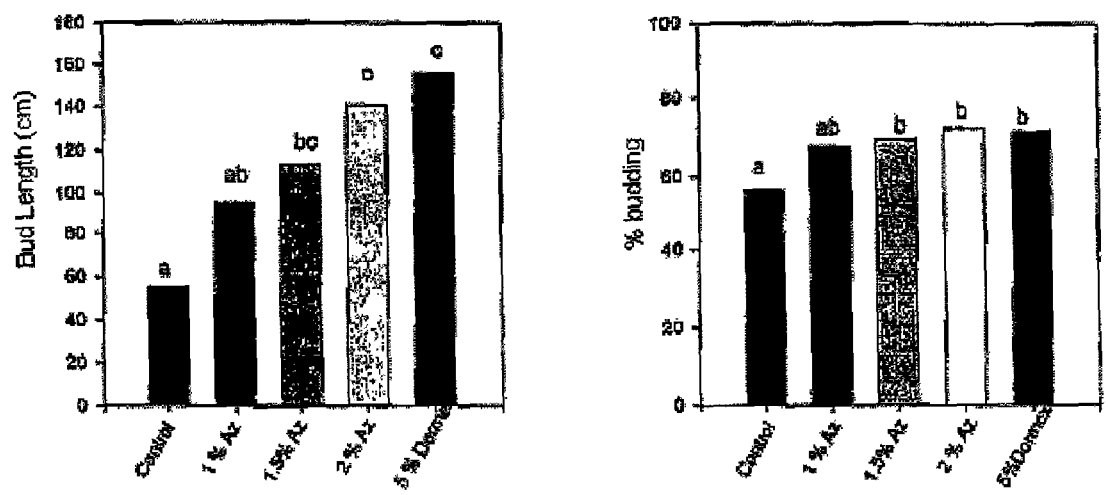
FIG. 3 are graphs showing the effect of the various doses of 1, 1.5 and 2% (w/v) sodium azide in aqueous solution on the bud length and on the budding percentage of cv. Thompson seedless grapevine; treatments were carried out on June 22 and a 5% Dormex (w/v) solution was used as a positive control and water as a negative control; different letters indicate significant statistical differences.

Field trials made in Vicuña (region IV) during 2003 season indicated that the induction of the budding by azide depends on the applied dose and that the penetration of the active compound into the bud is of vital importance to obtain the wished results. During 2005 season the field trials were repeated in Vicuña using higher doses of Azide. In these experiments doses of 1, 1.5 and 2% Azide aqueous and ammoniacal solution to 1% were used. Water was used as a negative control and Dormex 5% (2.5% $H_2CN_2$) as a positive control. The experimental design corresponded to completely randomized blocks with four replications by treatments and 8 treatments. The applications were made by aspersion in manual way on June 22 and the evaluations were made on August 24 and on September 21. FIG. 2 shows the effect of the different sodium azide dose 1; 1.5 and 2% (w/v) in aqueous and ammoniacal solution to 1% on the percentage of budding of cv. Thompson seedless grapevine buds evaluated on August 24. FIG. 3 shows the effect of the different sodium azide dose 1; 1.5 and 2% (w/v) in aqueous solution on the bud length and on the percentage of budding of cv. Thompson seedless grapevine buds evaluated on September 21. Different letters indicate statistically significant differences (ANOVA).

The greenhouse results the same as the field applications demonstrate the reproducibility of the inducer effect of $NaN_3$ on the budding of cv Thompson seedless grapevine buds. More even, it is demostrated that the effects depend on the applied dose and that at relatively low concentrations (1-2%) the wished effects are similar to Dormex.

INNOVATIVE ASPECT OF THE PRESENT INVENTION.

The new aspect of the present invention is that although many chemical compounds have been tested as potential inducers of the budding of deciduous fruit trees buds, no one has shown the power of $H_2CN_2$ and, precisely, this power is the main reason of the universal use of $H_2CN_2$. Consequently, we are at the first time in the presence of another compound ($NaN_3$) that at low concentrations induces the budding with the same efficiency as H2CN2 makes. The azide salts are the active principle (a.p.) of the compound which induces the budding and the ammonia added to the solution acts facilitating the penetration of the a.p. into the buds.

Both the low prices of sodium azide in Chinese market, U$ 10930×ton, and the low $NaN_3$ concentrations required to produce the wished effects allow to formulate an alternative product highly competitive when compared with DORMEX.

The invention claimed is:
1. A method for breaking dormancy of buds in deciduous fruit trees, comprising:
   spraying on buds of deciduous fruit trees an effective amount of an aqueous solution of alkali metal azide salt to induce budding, wherein the azide salt concentration is between approximately 0.2 and 5% (w/v), whereby the dormancy of the buds is broken.

2. The method of claim 1, wherein the aqueous solution further comprises ammonia at approximately 0.1 to 1% concentration.

3. The method of claim 2, wherein the alkali metal azide salt is selected from the group consisting of sodium azide and potassium azide, and the azide salt concentration is 1%, 1.5% or 2%.

4. The method of claim 3, wherein the ammonia concentration is 1%.

5. The method of claim 4, wherein the solution is free of ethanol.

6. The method of claim 2, wherein the solution is free of ethanol.

7. A composition for breaking dormancy of buds in deciduous fruit trees, consisting of:
dormant buds on a deciduous fruit tree,
wherein said buds have been sprayed with an aqueous solution consisting of alkali metal azide salt effective to induce budding, said azide salt having a concentration in solution between approximately 0.2 and 5% (w/v) and ammonia at approximately 0.1 to 1% concentration.

8. The composition of claim 7 wherein the alkali metal azide salt is selected from the group consisting of sodium azide and potassium azide, and the azide salt concentration is 1%, 1.5% or 2%.

9. The composition of claim 8, wherein the ammonia concentration is 1%.

10. The composition of claim 9, wherein the solution is free of ethanol.

* * * * *